United States Patent
Chomat et al.

(10) Patent No.: US 9,610,461 B2
(45) Date of Patent: Apr. 4, 2017

(54) COMBINATION OF A MC1R RECEPTOR AGONIST AND UVB FOR THE TREATMENT AND/OR PREVENTION OF PIGMENTATION DISORDERS

(71) Applicant: GALDERMA RESEARCH & DEVELOPMENT, Biot (FR)

(72) Inventors: Carole Chomat, Cagnes sur Mer (FR); Philippe Martel, Biot (FR); Johannes Voegel, Châteauneuf/Grasse (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 14/385,416

(22) PCT Filed: Mar. 15, 2013

(86) PCT No.: PCT/EP2013/055434
§ 371 (c)(1),
(2) Date: Sep. 15, 2014

(87) PCT Pub. No.: WO2013/135880
PCT Pub. Date: Sep. 19, 2013

(65) Prior Publication Data
US 2015/0045719 A1    Feb. 12, 2015

Related U.S. Application Data

(60) Provisional application No. 61/611,342, filed on Mar. 15, 2012.

(51) Int. Cl.

| | | |
|---|---|---|
| *A61K 38/00* | (2006.01) | |
| *A61N 5/06* | (2006.01) | |
| *A61K 38/33* | (2006.01) | |
| *A61K 38/34* | (2006.01) | |
| *A61K 38/35* | (2006.01) | |
| *A61K 45/06* | (2006.01) | |
| *A61K 31/397* | (2006.01) | |
| *A61K 31/40* | (2006.01) | |
| *A61K 31/445* | (2006.01) | |
| *A61K 31/4178* | (2006.01) | |
| *A61K 31/4196* | (2006.01) | |
| *A61K 31/435* | (2006.01) | |
| *A61K 31/454* | (2006.01) | |

(52) U.S. Cl.
CPC ............ *A61N 5/062* (2013.01); *A61K 31/397* (2013.01); *A61K 31/40* (2013.01); *A61K 31/4178* (2013.01); *A61K 31/4196* (2013.01); *A61K 31/435* (2013.01); *A61K 31/445* (2013.01); *A61K 31/454* (2013.01); *A61K 38/33* (2013.01); *A61K 38/34* (2013.01); *A61K 38/35* (2013.01); *A61K 45/06* (2013.01); *A61N 5/0614* (2013.01); *A61N 2005/0661* (2013.01); *F04C 2270/041* (2013.01)

(58) Field of Classification Search
CPC .. A61K 2300/00; A61K 31/397; A61K 31/40; A61K 31/445; A61K 38/33; A61K 38/34; A61K 38/35; A61K 31/00; A61K 31/4178; A61K 31/4196; A61K 31/435; A61K 31/454; A61K 45/06; A61K 38/00
See application file for complete search history.

(56) References Cited

U.S. PATENT DOCUMENTS

| 8,871,187 B2* | 10/2014 | Bouix-Peter ......... A61K 8/4906 424/70.1 |
|---|---|---|
| 9,353,083 B2* | 5/2016 | Bouix-Peter ........... A61Q 19/00 |
| 2011/0130705 A1* | 6/2011 | Wolgen ................ A61K 9/0019 604/20 |
| 2013/0203670 A1* | 8/2013 | Wolgen .................. A61K 38/34 514/10.7 |
| 2014/0228342 A1* | 8/2014 | Bouix-Peter ........... A61Q 19/00 514/210.18 |
| 2016/0237065 A1* | 8/2016 | Bouix-Peter ........... A61Q 19/00 |

FOREIGN PATENT DOCUMENTS

| WO | 8704623 A1 | 8/1987 |
|---|---|---|
| WO | 2010052253 A1 | 5/2010 |
| WO | 2010052255 A1 | 5/2010 |
| WO | 2010096853 A1 | 9/2010 |

OTHER PUBLICATIONS

Anbar et al. Skin pigmentation after NB-UVB and three analogues of prostaglandin F2alpha in guinea pigs: a comparative study. JEADV 2010, vol. 24, pp. 28-31.*
Berneburg et al. Phototherapy with Narrowband UVB. Acta Derm Venereol. 2005, vol. 85, pp. 1-11.*
International Search Report and Written Opinion dated Aug. 5, 2013 corresponding to International Patent Application No. PCT/EP2013/055434, 8 pages.

* cited by examiner

*Primary Examiner* — Marcela M Cordero Garcia
(74) *Attorney, Agent, or Firm* — Dentons US LLP (57) ABSTRACT

A system comprising a combination of at least one MC1R receptor agonist and a source of NB-UVB, wherein said system is adapted for simultaneous or sequential use of said MC1R receptor agonist and said NB-UVB in amounts effective for the treatment and/or prevention of dermatological conditions linked to a hypopigmentation.

15 Claims, 2 Drawing Sheets

Measurement of pigmentation by image analysis at study end
Test t Student versus vehicle /
Test t de student versus AVB 60mJ/cm² - vehicle

COMBINATION OF A MC1R RECEPTOR AGONIST AND UVB FOR THE TREATMENT AND/OR PREVENTION OF PIGMENTATION DISORDERS

CROSS-REFERENCE TO PRIOR APPLICATIONS

This application is a National Stage of PCT/EP2013/055434, filed Mar. 15, 2013, and designating the United States (published in English on Sep. 19, 2013, as WO 2013/135880 A1), which claims priority under 35 U.S.C. §119 to U.S. Provisional Patent Application No. 61/611,342, filed Mar. 15, 2012, each hereby expressly incorporated by reference in its entirety and each assigned to the assignee thereof.

The invention relates to compounds used in phototherapy for the treatment and/or prevention of dermatological conditions associated with hypopigmentation. The pigmentation of human skin results from the synthesis of melanin by melanocytes. Melanocytes contain organelles called melanosomes, head of melanin biosynthesis and, more specifically, two chemically distinct kinds of melanin, eumelanin, a pigment-brown and black, phaeomelanin, a pigment of yellow-red color. The melanin synthesis or melanogenesis schematically involves the following main steps:
Tyrosine→dopa→quinone→Dopachrome→Melanin.

Within the melanosomes, tyrosinase is the key enzyme of melanogenesis. It is synthesized as an inactive precursor, which is activated when the melanocytes are stimulated by α-MSH via cAMP. Tyrosinase catalyzes the first two steps with the hydroxylation of tyrosine to 3,4-dihydroxyphenylalanine (DOPA) and oxidation of DOPA (non-free intermediate of the catalytic reaction) in DOPAquinone.

All individuals, regardless of skin type, have approximately the same number of melanocytes in a given unaffected skin area. The differences in pigmentation are not due to the number of melanocytes, but the properties of their melanosomes. In humans, as in other mammals, the skin color and hair is mainly determined by the number, size, type and mode of distribution of melanosomes. Melanin is deposited uniformly on the internal network of fibrillar melanosome and opacity of the organelle increases until saturation. Gradually, as melanin is synthesized in melanosomes, they move to the perinuclear region towards the end of the dendrites of melanocytes. These are the melanosomes which, after migration along the dendrites, are transferred from melanocytes to keratinocytes and redistributed in keratinocytes. The keratinocytes are then transported to the surface of the skin in the process of differentiation of the epidermis and melanin is well distributed in the epidermis, ensuring its protection and its browning (Gilchrest B A, Park H Y, Eller M S, Yaar M. Mechanisms of ultraviolet light-induced pigmentation. Photochem Photobiol 1996, 63: 1-10; Hearing V J, Tsukamoto K, Enzymatic control of pigmentation in mammals. FASEB J 1991; 5: 2902-2909).

Although the amount of melanin varies from one population to another, the amount of tyrosinase does not vary significantly and the level of tyrosinase mRNA is identical in white or black skins.

Changes in melanogenesis are particularly due to variations in the activity of melanocytes and tyrosinase primarily, in the type of melanin synthesized, and the ability of keratinocytes phagocytose melanosomes and partition into the skin. Moreover, we know that the natural pigmentation can be modulated by many factors intrinsic or extrinsic. The amount and nature of melanin contained in human skin, and their distribution, are influenced by various factors such as heredity or by exposure to physical agents such as X-rays, UV, burning, cold and other mechanical or chemical agents to depigmenting agents such as topical corticosteroids, azelaic acid, benzoyl peroxide, hydroquinone.

Among the various possible causes of skin hypopigmentation, one can distinguish diffuse or circumscribed hereditary hypopigmentation and hypopigmentation acquired, not genetically determined, circumscribed.

Specifically, Vitiligo is a chronic disease of the skin characterized by the appearance of spots of a dull white to precise contour on the feet, hands, face, lips or other body parts. Depigmentation may be more or less, and depigmented areas, of varying sizes. Vitiligo is a disease characterized by destruction of melanocytes that occurs mainly in the skin and results in the appearance of well circumscribed white macules. The exact pathophysiologic mechanism that leads to the destruction of melanocytes is still elusive, and involves autoimmunity in the pathogenesis of vitiligo (Passeron T, Ortonne J P 2005; Spritz 2007).

Vitiligo is common and affects 1% to 2% of the general population. For many patients with vitiligo, the disfigurement caused by the disease has a great impact on their quality of life (Ongenae K et al. 2006). Vitiligo is an area of unmet therapeutic need. Currently, there are several therapeutic modalities that can be proposed for the treatment of vitiligo. However, it is still very difficult to compare the efficacy of different treatment modalities and the results of different studies on the same treatment because: (i) most published studies are uncontrolled; and (ii) there is not a generally accepted biometric tool to assess disease severity and response to treatment.

There are two types of vitiligo:
Segmental vitiligo localized unilaterally on an area of the face, upper body, legs or arms, which usually does not evolve;
Generalized vitiligo, which often presents spots more or less symmetric bilateral areas of friction or pressure that can be repeated and more important over the years. People with vitiligo have a greater probability of developing other autoimmune diseases. Depigmentation observed in vitiligo results from the disappearance of melanocytes in lesional areas. Several causes are responsible for this disorder: autoimmune autocytotoxique, neural dysfunction (Passeron and Ortonne, 2005).

In the context of normal skin, melanocyte survival, proliferation, and differentiated function are influenced by UV irradiation. UV irradiation induces tanning, so-called facultative skin color, an increase above baseline of constitutive skin pigmentation that provides protection against future UV irradiation. Tanning is divided into immediate tanning and delayed tanning. Immediate tanning, or immediate pigment darkening, occurs within 5 to 10 minutes of exposure and fades within minutes to days depending on the UV dose and the complexion of the individual. Immediate tanning does not provide photoprotection and does not increase epidermal melanin level. It is primarily produced by UVA irradiation, although visible light can also induce immediate tanning. Immediate tanning is only visible in darker individuals and is of greyish-brown color, and it is thought to represent melanosomal relocation from the perikaryon to melanocyte dendrites. Delayed tanning occurs within 3 to 4 days after UV exposure. Delayed tanning is affected by both UVB and UVA. The action spectrum that produces delayed tanning is the same as for UV-induced erythema (sunburn), with UVB wavelengths far more effective than UVA. Especially in darker-skinned individuals, sub-erythemogenic UV doses may be effective as well. Delayed tanning peaks between 10 days and 3 to 4 weeks, depending on the absorbed UV dose and the individuars skin type, then fades gradually over a few weeks. Histologically, there are increased epidermal melanocytes, melanocyte dendricity, and melanosome transfer to keratinocytes, with greater melanization of individual melanosomes. Overall, total epidermal melanin is increased, providing additional photoprotection from UV irradiation.

In the context of Vitiligo, Psoralen plus ultraviolet (UV) A (PUVA) photochemotherapy and topical corticosteroids have been, for a long time, the backbone of treatment of vitiligo (Antoniou C, Katsambas A 1992). In 1997, however, a first report was published by Westerhof (Westerhof W, Nieuweboer-Krobotova L 1997) on the use of narrowband (NB) UVB phototherapy for the treatment of vitiligo. NB UVB light source emits polychromatic light, but the 311- to 313-nm wavelength range predominates in its emission spectrum. NB-UVB was introduced approximately 10 years before the above report for the treatment of psoriasis, after the observation that wavelengths around 311 nm provoked less erythema and, at the same time, were most effective for complete clearance of psoriasis lesions (Parrish J A, Jaenicke K F 1981).

Ultraviolet rays are classified in three categories according to their wavelength: UVA wavelength between 315 and 400 nm, UVB wavelength between 280 and 315 nm, and UVC wavelength between 100 and 280 nm. UV-induced immediate response and a later response. Immediate action, minutes after treatment, persists for several days but this rapid increase in pigmentation results only from the oxidation of pre-existing pigments and redistribution of melanosomes without an increase in melanogenesis. The late response to UV is an increase of melanogenesis, which results from increased expression of MITF, a major regulator of transcription of pigmentation and the downstream targets including PMEL17, MART-1, tyrosinase, TYRP1, Tyrp2/Dct. In addition, epidermal melanocytes and keratinocytes also respond to UV exposure by increasing their production in α-MSH and ACTH, which, in turn, induce increased expression of MC1R on the surface of melanocytes and thus stimulate melanogenesis (Mr. Demarchez, and melanocyte pigmentation, Biology of Skin, 2011).

Melanocortin peptide hormones are involved in diverse physiological processes such as pigmentation, adrenal function, energy homeostasis, and immune and sexual function. To date, five melanocortin receptors (MC1R to MC5R) have been identified, which differ in their tissue distributions, functions and affinities to different melanocortins (Abdel-Malek 2001; Maaser et al. 2006; Voisey et al. 2003).

MC1R is predominantly expressed by melanocytes but is also present in a number of non-melanocytic cells, including immune cells (e.g. neutrophils, monocytes), endothelial cells and fibroblasts. The activity of MC1R is modulated by the endogenous agonists, alpha-melanocyte stimulating hormone (α-MSH) and adrenocorticotropic hormone (ACTH), and endogenous antagonist agouti signalling protein (ASP) (Wilson et al. 2006).

MC1R signalling plays a key role in the regulation of mammalian skin and hair colour. Addition of an MC1R agonist to cultured human melanocytes stimulates proliferation and melanogenesis, protects against UV-induced apoptosis, enhances repair of UV-induced DNA damage and reduces oxidative stress (Rouzaud et al. 2005). Allelic MC1R gene variants are associated with red hair and pale skin in humans and with lighter hair colour in mice (Robbins et al. 1993). Injection of potent α-MSH peptide analogues results in darker skin in humans and darker hair in mice due to increased production of eumelanin (Hadley M E, Dorr R T 2006).

As MC1R agonists stimulate melanocyte proliferation and melanogenesis, topical treatment with a MC1R agonist may be effective in vitiligo.

We know the document FR2937973 patent and WO2010/052253, which disclose MC1R modulating compounds used to treat pigmentation disorders, both hypopigmentation and hyperpigmentation, inflammation and immune and incorporated by reference.

Considering the above, a problem to be solved by the invention is to provide an improved treatment of dermatological conditions associated with hypopigmentation increasing melanogenesis.

As part of the invention, increased melanogenesis is characterized by an immediate response and a later response by stimulating the natural ways of pigmentation and increased activity of these pathways.

The present invention provides a system comprising a combination of at least one MC1R receptor agonist and a source of NB-UVB, wherein said system is adapted for simultaneous or sequential of said MC1R receptor agonist and said NB-UVB in amounts effective for the treatment and/or prevention of dermatological conditions linked to a hypopigmentation.

Accordingly, said MC1R agonist is preferably selected from the melanocyte stimulating hormones (MSH) α, β or γ, adrenocorticotropic hormone (ACTH) 1-39, the β-lipotropin, the β-endorphin and compounds of general formula (I) or (II):

wherein R1, R2, R3, R4, R5, X and n and m for formula (I) have the meaning described below and R1, R2, R3, R4, R5 for the general formula (II) have also the meaning as defined below and include salts and enantiomers of compounds of general formula (I) and/or (II) where appropriate In a specific embodiment of the invention, said MC1R agonist is selected from compounds of formula (II), wherein:
R1 is a cyclopropylmethyl group or a 4-hydroxybutyl;
R2 represents a hydrogen atom, a methyl group; and respective salts and enantiomers.

The system according to the invention comprises said MC1R agonist in a composition applied topically or administered orally.

In one embodiment, said the composition comprises, in a cosmetically acceptable medium, at least one MC1R agonist, preferentially at least a compound of general formula (I) or (II).

In the context of the invention, said MC1R agonist is present in composition at a concentration between about 0.001 and 10% by weight based on the total weight of the composition comprising it.

In a particular embodiment, the NB-UVB length wave is selected between 280 and 315 nm, and preferentially between 305 nm and 310 nm, most preferred between 307 nm and 309 nm.

The system according to claim 1, wherein the skin disease associated with hypopigmentation is selected from vitiligo, albinism, the hypomelanoses, the depigmentation by physical or chemical agents, the post-inflammatory hypopigmentation, the phenomenon of Sutton or other hypopigmentation lesions.

The present invention also relates to the use of a composition comprising at least one MC1R receptor agonist in combination with NB-UVB, for simultaneous or sequential in time for the treatment and/or prevention of dermatological conditions linked to a hypopigmentation. The features of MC1R agonist and the NB-UVB are as described though out the specification.

The present invention also relates to a method for treating and/or preventing of dermatological conditions linked to hypopigmentation comprising applying to an affected or susceptible area, a combination of at least one MC1R receptor agonist and NB-UVB for simultaneously or sequentially in time for the treatment and/or prevention of dermatological conditions linked to a hypopigmentation. The features of MC1R agonist and the NB-UVB are as described though out the specification.

More specifically, the skin disease associated with hypopigmentation is selected from vitiligo, albinism, the hypomelanoses, the depigmentation by physical or chemical agents, the post-inflammatory hypopigmentation, the phenomenon of Sutton or other hypopigmentation lesions, preferably vitiligo.

In another embodiment, the present invention relates to a product containing a composition comprising at least one MC1R receptor agonist for use in combination with NB-UVB, as a medicament for simultaneous or sequential in time for the treatment and/or prevention of dermatological conditions linked to a hypopigmentation.

The invention and its benefits will be better understood upon reading the description and the embodiments following but in a non-limiting manner.

Hypopigmentation according to the invention means a decrease in the usual color of the skin, hair or hair, or discoloration resulting in total depigmentation characterized by the absence of melanocytes in the affected area. The skin disease associated with hypopigmentation of the invention is preferably selected from vitiligo, albinism, the hypomélanoses, the depigmentation by physical or chemical agents, the postinflammatory hypopigmentation, the phenomenon of Sutton or other hypopigmentation lesions, yet more preferably vitiligo.

The MC1R receptor agonist according to the invention is preferably selected from the melanocyte stimulating hormones (MSH) α, β or γ, adrenocorticotropic hormone (ACTH) 1-39, the β-lipotropin, the β-endorphin and compounds of general formula (I) or (II):

(I)

(II)

wherein for formula (I):
R1 represents a hydrogen atom, aryl, substituted aryl, alkyl, cycloalkyl, cycloalkylalkyl, or cycloalkylalkylalkyle;
R2 represents a hydrogen atom, hydroxy, lower alkyl, substituted lower alkyl, higher alkyl, higher alkyl substituted cycloalkyl, cycloalkylalkyl, lower alkoxy, substituted lower alkoxy, higher alkoxy, substituted higher alkoxy, a cycloalkylalkoxy, acyloxy, acyl, alkoxycarbonyl, carboxamide, carboxylic acid, cyano, amino or disubstituted by acyl and aryl or alkyl;
R3 represents aralkyl or substituted aralkyl;
R 4 represents a heteroaryl or a substituted heteroaralkyl;
R5 represents a hydrogen atom or alkyl;
X represents an oxygen atom or a sulfur atom;
n, m may be equal to 1 or 2;
and salts and corresponding enantiomers.
wherein for the general formula (II):
R1 represents an aryl, substituted aryl or cycloalkyl;
R2 represents a hydrogen atom, hydroxy, lower alkyl, substituted lower alkyl, higher alkyl, higher alkyl substituted cycloalkyl, cycloalkylalkyl, lower alkoxy, substituted lower alkoxy, higher alkoxy, substituted higher alkoxy, a cycloalkylalkoxy, or acyloxy:
R3 represents aralkyl or substituted aralkyl;
R 4 represents a heteroaralkyl, substituted heteroaralkyl, heteroalkyl or substituted heteroalkyl;
R 5 represents a hydrogen atom, hydroxy, amino, acylamino or a sulfonamide; and salts and enantiomers of compounds of general formula (II) where appropriate Among the addition salts of the compounds of general formula (I) or (II) with a pharmaceutically acceptable acid include salts with preferably an organic acid or with an inorganic acid.

Suitable inorganic acids are, for example hydrohalic acids such as hydrochloric acid or hydrobromic acid, sulfuric acid, nitric acid.

Suitable organic acids are, for example picric acid, methanesulfonic acid, ethane sulfonic acid, paratoluene sulphonic acid, oxalic acid, tartaric acid.

The compounds of general formula (I) or (II), may also exist in forms of hydrates or solvates with water or with a solvent.

Suitable solvents to form hydrates or solvates are for example alcohols such as ethanol or isopropanol or water.

According to the present invention, aryl refers, in particular, phenyl or naphthyl unsubstituted.

According to the present invention, substituted aryl means, in particular, phenyl or naphthyl substituted with one or more groups of atoms selected from alkyl, alkoxy, halogen, hydroxy, cyano, trifluoromethyl and nitro.

According to the present invention, a cycloalkyl designates, in particular, a saturated hydrocarbon chain, cyclic, containing from 3 to 7 carbon atoms.

According to the present invention, hydroxy means the hydroxyl group OH.

According to the present invention, amino refers to the amino group NH2.

According to the present invention, cyano means the cyano group CN.

According to the present invention, carboxylic acid refers to, in particular, the CO2H group.

According to the present invention, acyl means, in particular, a formyl or carbonyl substituted with alkyl, cycloalkyl or cycloalkylalkyl.

According to the present invention, alkyl means, in particular, lower alkyl or a higher alkyl substituted or unsubstituted.

According to the present invention, lower alkyl means, in particular, a saturated hydrocarbon chain, unsaturated, linear or branched, containing from 1 to 4 carbon atoms or an unsaturated hydrocarbon chain comprising from 2 to 4 carbon atoms including for example methyl, ethyl, propyl, isopropyl, butyl.

According to the present invention, substituted lower alkyl means, in particular, a saturated hydrocarbon chain, unsaturated, linear or branched, containing from 1 to 4 carbon atoms and substituted with one or more halogen atoms or hydroxy, or unsaturated hydrocarbon chain comprising from 2 to 4 carbon atoms and substituted with one or more halogen atoms or hydroxy.

According to the present invention, a higher alkyl means, in particular, a saturated hydrocarbon chain, unsaturated, linear or branched, comprising from 5 to 10 carbon atoms.

According to the present invention, a higher alkyl substituted means, in particular, a saturated hydrocarbon chain, unsaturated, linear or branched, comprising from 5 to 10 carbon atoms and substituted with one or more halogen atoms or hydroxy.

According to the present invention, halogen atom means, in particular, chlorine, fluorine, iodine and bromine atoms.

According to the present invention, cycloalkylalkyl means, in particular, alkyl substituted by cycloalkyl.

According to the present invention, a lower alkoxy means, in particular, an oxygen atom substituted by lower alkyl and, in particular, methoxy, ethoxy, propoxy, isopropoxy, butoxy.

According to the present invention, a substituted lower alkoxy means, in particular, an oxygen atom substituted with a substituted lower alkyl.

According to the present invention a higher alkoxy means, in particular, an oxygen atom substituted higher alkyl.

According to the present invention, a substituted higher alkoxy means, in particular, an oxygen atom substituted higher alkyl, which is substituted.

According to the present invention, a cycloalkylalkoxy means, in particular, an oxygen atom substituted cycloalkylalkyl.

According to the present invention, acyloxy means, in particular, an oxygen atom substituted with acyl.

According to the present invention, an alkoxycarbonyl means, in particular, a carbonyl substituted by an alkoxy, cycloalkoxy or cycloalkylalkoxy.

According to the present invention, carboxamide means, in particular, a carbonyl substituted with a mono- or di-alkylamino.

According to the present invention, aralkyl means, in particular, alkyl substituted with aryl.

According to the present invention, a substituted aralkyl means, in particular, alkyl substituted with substituted aryl.

According to the present invention, heterocycle means, in particular, a cyclic or bicyclic hydrocarbon chain, saturated or unsaturated, comprising one or more heteroatoms chosen from O, S and N.

According to the present invention, substituted heterocycle means, in particular, a cyclic or bicyclic hydrocarbon chain, saturated or unsaturated, comprising one or more heteroatoms chosen from O, S and N substituted with one or more alkyl groups.

According to the present invention, heteroaryl means, in particular, an aromatic heterocycle.

According to the present invention, substituted heteroaryl means, in particular, an aromatic heterocycle substituted with one or more alkyl groups.

According to the present invention, heteroaralkyl means, in particular, a substituted alkyl heteroaryl.

According to the present invention, a substituted heteroaralkyl refers, in particular, alkyl substituted by a substituted heteroaryl.

Preferentially for compounds of formula (II):
R1 is a cyclopropylmethyl group or a 4-hydroxybutyl;
R2 represents a hydrogen atom, a methyl group.

The MC1R receptor agonist according to the invention is more preferably selected from compounds of general formula (I):

1-[(S)-2-(4-Butyryl-4-phenyl-piperidin-1-yl)-1-(4-methoxy-benzyl)-2-oxo-ethyl]-3-[2-(1H-imidazol-4-yl)-ethyl]-urea;

1-[2-(1H-Imidazol-4-yl)-ethyl]-3-[1-(4-methoxy-benzyl)-2-oxo-2-(4-oxo-1-phenyl-1,3,8-triaza-spiro[4.5]dec-8-yl)-ethyl]urea;

1-[2-(4-Cyano-4-phenyl-piperidin-1-yl)-1-(4-methoxy-benzyl)-2-oxo-ethyl]-3-[2-(1H-imidazol-4-yh-ethyl]-urea;
1-[2-(1H-Imidazol-4-yl)-ethyl]-3-[1-(4-methoxy-benzyl)-2-oxo-2-(4-phenyl-piperidin-1-yl)-ethyl]-urea;

1-[2-(1H-Imidazol-4-yh-ethyl]-3-[1-(4-methoxy-benzyl)-2-oxo-2-piperidin-1-yl-ethyl]-urea;

4-Cyclohexyl-1-[2-{3-[2-(1H-imidazol-4-yh-ethyl]-ureido}-3-(4-methoxy-phenyl)-propionyl]-piperidine-4-ethyl-carboxylate;

N-{1-[2-{3-[2-(1H-Imidazol-4-yh-ethyl]-ureido}-3-(4-methoxy-phenyl)-propionyl]-piperidin-4-yl}-N-phenyl-propionamide;

1-[2-{3-[2-(1H-imidazol-4-yh-ethyl]-ureido}-3-(4-methoxy-phenyl)-propionyl]-3-phenyl-azetidin-3-yl-butyrate;

1-[2-{3-[2-(1H-Imidazol-4-yh-ethyl]-ureido}-3-(4-methoxy-phenyl)-propionyl]-piperidine-4-ethyl-carboxylate;

1-[2-(1H-Imidazol-4-yl)-ethyl]-3-{1-(4-methoxy-benzyl)-2-[4-(2-methoxy-phenyl)-piperidin-1-yl]-2-oxo-ethyl}-urea;

1-[2-(3-Butoxy-3-phenyl-azetidin-1-yl)-1-(4-methoxy-benzyl)-2-oxo-ethyl]-3-[2-(1H-imidazol-4-yl)-ethyl]-urea;

4-Cyclohexyl-1-[2-{3-[2-(1H-imidazol-4-yh-ethyl]-ureido}-3-(4-methoxy-phenyl)-propionyl]-piperidine-4-methyl-carboxyamide;

1-[2-(3-Cyclohexanecarbonyl-azetidin-1-yl)-1-(4-methoxy-benzyl)-2-oxo-ethyl]-3-[2-(1H-imidazol-4-yl)-ethyl]-urea; 4-Cyclohexyl-1-[2-{3-ethyl-3-[2-(1H-imidazol-4-yl)-ethyl]-ureido}-3-(4-methoxy-phenyl)-propionyl]-piperidine-4-ethyl-carboxylate; N-Cyclopropyl-N-{1-[2-{3-[2-(1H-imidazol-4-yl)-ethyl]-ureido}-3-(4-methoxy-phenyl)-propionyl]-piperidin-4-yl}-propionamide;

4-Cyclohexyl-1-(2-{3-[2-(1H-imidazol-4-yh-ethyl]-ureido}-3-phenyl-propionyl)-piperidine-4-ethyl-carboxylate;

1-[2-(4-Butyryl-4-cyclohexyl-piperidin-1-yl)-1-(4-methoxy-benzyl)-2-oxo-ethyl]-3-[2-(3H-imidazol-4-yl)-ethyl]-urea;

1-[2-(4-Butoxy-4-cyclohexyl-piperidin-1-yl)-1-(4-methoxy-benzyl)-2-oxo-ethyl]-3-[2-(1H-imidazol-4-yl)-ethyl]-urea;
4-Cyclohexyl-1-(2-{3-[2-(1H-imidazol-4-yl)-ethyl]-ureido}-2-phenyl-acetyl)-piperidine-4-ethyl-carboxylate;
4-Cyclohexyl-1-[2-{3-[2-(1H-imidazol-4-yl)-ethyl]-ureido}-3-(4-methoxy-phenyl)-propionyl]-piperidine-4-methyl-carboxylate;
1-[2-(4-Cyclohexyl-4-ethoxy-piperidin-1-yl)-1-(4-methoxy-benzyl)-2-oxo-ethyl]-3-[2-(1H-imidazol-4-yl)-ethyl]-urea;
1-[2-(4-Acetyl-4-cyclohexyl-piperidin-1-yl)-1-(4-methoxy-benzyl)-2-oxo-ethyl]-3-[2-(1H-imidazol-4-yl)-ethyl]-urea;
4-Cyclohexyl-1-(2-{3-[2-(1H-imidazol-4-yl)-ethyl]-ureido}-2-phenyl-acetyl)-piperidine-4-methyl-carboxylate;
4-Ethyl-1-[2-{3-[2-(1H-imidazol-4-yl)-ethyl]-ureido}-3-(4-methoxy-phenyl)-propionyl]-piperidine-4-ethyl-carboxylate;
1-[2-(4-Cyclohexyl-4-propoxy-piperidin-1-yl)-1-(4-methoxy-benzyl)-2-oxo-ethyl]-3-[2-(1H-imidazol-4-yl)-ethyl]-urea;
4-cyclohexyl-1-[2-{3-[2-(1H-imidazol-4-yl)-ethyl]-ureido}-3-(4-methoxy-phenyl)-propionyl]-piperidine-4-carboxylic acid;
1-[2-(1H-imidazol-4-yl)-ethyl]-3-{1-(4-methoxy-benzyl)-2-[3-(2-methyl-cyclohexyl)-3-propoxy-azetidin-1-yl]-2-oxo-ethyl}-urea;
4-Cyclohexyl-1-[2-{3-[2-(1H-imidazol-4-yl)-ethyl]-ureido}-3-(4-methoxy-phenyl)-propionyl]-piperidine-4-propyl-carboxylate;
1-[2-(1H-Imidazol-4-yl)-ethyl]-3-[1-(4-methoxy-benzyl)-2-oxo-2-(3-pentyl-3-phenyl-azetidin-1-yl)-ethyl]-urea;
1-((R)-3-(4-Chloro-phenyl)-2-{3-[2-(1H-imidazol-4-yl)-ethyl]-ureido}-propionyl)-4-cyclohexyl-piperidine-4-ethyl-carboxylate;
1-((S)-3-(4-Chloro-phenyl)-2-{3-[2-(1H-imidazol-4-yl)-ethyl]-ureido}-propionyl)-4-cyclohexyl-piperidine-4-ethyl-carboxylate;
1-[2-(4-Cyclohexyl-4-propionyl-piperidin-1-yl)-1-(4-methoxy-benzyl)-2-oxo-ethyl]-3-[2-(1H-imidazol-4-yl)-ethyl]-urea;
1-[2-(4-Cyclohexyl-4-propionyl-piperidin-1-yl)-1-(4-methoxy-benzyl)-2-oxo-ethyl]-3-(1H-imidazol-4-ylmethyl)-urea;
4-Cyclohexyl-1-[(R)-2-{3-[2-(1H-imidazol-4-yl)-ethyl]-ureido}-3-(4-methoxy-phenyl)-propionyl]-piperidine-4-ethyl-carboxylate;
4-Cyclopropylmethyl-1-[2-{3-[2-(1H-imidazol-4-yl)-ethyl]-ureido}-3-(4-methoxy-phenyl)-propionyl]-piperidine-4-ethyl-carboxylate;
4-Cyclohexyl-1-(2-{3-[2-(1H-imidazol-4-yl)-ethyl]-ureido}-3-phenyl-propionyl)-piperidine-4-propyl-carboxylate;
4-Cyclopentyl-1-(2-{3-[2-(1H-imidazol-4-yl)-ethyl]-ureido}-3-phenyl-propionyl)-piperidine-4-ethyl-carboxylate;
4-Cyclopentyl-1-[2-{3-[2-(1H-imidazol-4-yl)-ethyl]-ureido}-3-(4-methoxy-phenyl)-propionyl]-piperidine-4-ethyl-carboxylate;
4-Cyclohexyl-1-[(S)-2-{3-[2-(1H-imidazol-4-yl)-ethyl]-ureido}-3-(4-methoxy-phenyl)-propionyl]-piperidine-4-ethyl-carboxylate;
1-[(R)-2-(4-Butyryl-4-cyclohexyl-piperidin-1-yl)-1-(4-methoxy-benzyl)-2-oxo-ethyl]-3-[2-(1H-imidazol-4-yl)-ethyl]-urea;
1-[(R)-2-(4-Butyryl-4-cyclohexyl-piperidin-1-yl)-1-(4-fluoro-benzyl)-2-oxo-ethyl]-3-[2-(1H-imidazol-4-yl)-ethyl]-urea;
1-[(R)-1-Benzyl-2-(4-butyryl-4-cyclohexyl-piperidin-1-yl)-2-oxo-ethyl]-3-[2-(1H-imidazol-4-yl)-ethyl]-urea;
1-[(R)-2-(4-Butyryl-4-cyclohexyl-piperidin-1-yl)-1-(4-methoxy-benzyl)-2-oxo-ethyl]-3-[2-(3-methyl-3H-imidazol-4-yl)-ethyl]-urea;
1-[(R)-2-(4-Butyryl-4-cyclohexyl-piperidin-1-yl)-1-(4-chloro-benzyl)-2-oxo-ethyl]-3-[2-(1H-imidazol-4-yl)-ethyl]-urea;
4-Cyclohexyl-1-((R)-3-(3,4-dichloro-phenyl)-2-{3-[3-(1H-imidazol-4-yl)-propyl]-ureido}-propionyl)-piperidine-4-ethyl-carboxylate;
4-Cyclohexyl-1-((R)-3-(4-methoxy-phenyl)-2-{3-[2-(3-methyl-3H-imidazol-4-yl)-ethyl]-ureido}-propionyl)-piperidine-4-ethyl-carboxylate;
4-Cyclohexyl-1-[(R)-2-{3-[2-(1H-imidazol-4-yl)-ethyl]-thioureido}-3-(4-methoxy-phenyl)-propionyl]-piperidine-4-ethyl-carboxylate;
1-[(R)-2-(4-Butyryl-4-cyclohexyl-piperidin-1-yl)-1-(4-methoxy-benzyl)-2-oxo-ethyl]-3-[2-(1H-imidazol-4-yl)-ethyl]-thiourea;
1-[(R)-2-(4-Cyclohexyl-4-propoxy-piperidin-1-yl)-1-(4-methoxy-benzyl)-2-oxo-ethyl]-3-[2-(1H-imidazol-4-yl)-ethyl]-thiourea;
1-[(R)-1-Benzyl-2-(4-cyclohexyl-4-propoxy-piperidin-1-yl)-2-oxo-ethyl]-3-[2-(1H-imidazol-4-yl)-ethyl]-thiourea;
1-[(R)-1-Benzyl-2-(4-cyclohexyl-4-propoxy-piperidin-1-yl)-2-oxo-ethyl]-3-[2-(1H-imidazol-4-yl)-ethyl]-urea;
4-Cyclohexyl-1-((R)-3-(4-methoxy-phenyl)-2-{3-[2-(3-methyl-3H-imidazol-4-yl)-ethyl]-thioureido}-propionyl)-piperidine-4-ethyl-carboxylate;
4-Cyclohexyl-1-((R)-2-{3-[2-(3-methyl-3H-imidazol-4-yl)-ethyl]-ureido}-3-phenyl-propionyl)-piperidine-4-ethyl-carboxylate;
1-[(R)-2-(4-Cyclohexyl-4-propoxy-piperidin-1-yl)-1-(4-methoxy-benzyl)-2-oxo-ethyl]-3-[2-(3-methyl-3H-imidazol-4-yl)-ethyl]-urea;
1-((R)-3-(4-Chloro-phenyl)-2-{3-[2-(3-methyl-3H-imidazol-4-yl)-ethyl]-ureido}-propionyl)-4-cyclohexyl-piperidine-4-ethyl-carboxylate;
4-Cyclohexyl-1-((R)-3-(4-fluoro-phenyl)-2-{3-[2-(3-methyl-3H-imidazol-4-yl)-ethyl]-ureido}-propionyl)-piperidine-4-ethyl-carboxylate;
4-Cyclohexyl-1-((R)-3-(4-fluoro-phenyl)-2-{3-[2-(1H-imidazol-4-yl)-ethyl]-ureido}-propionyl)-piperidine-4-ethyl-carboxylate;
4-Cyclohexyl-1-((R)-3-(4-fluoro-phenyl)-2-{3-[2-(1H-imidazol-4-yl)-ethyl]-thioureido}-propionyl)-piperidine-4-ethyl-carboxylate;
1-((R)-3-(4-Chloro-phenyl)-2-{3-[2-(1H-imidazol-4-yl)-ethyl]-thioureido}-propionyl)-4-cyclohexyl-piperidine-4-ethyl-carboxylate;
1-((R)-3-(4-Chloro-phenyl)-2-{3-[2-(3-methyl-3H-imidazol-4-yl)-ethyl]-thioureido}-propionyl)-4-cyclohexyl-piperidine-4-ethyl-carboxylate;
1-[(R)-2-(4-Cyclohexyl-4-propoxy-piperidin-1-yl)-1-(4-fluoro-benzyl)-2-oxo-ethyl]-3-[2-(1H-imidazol-4-yl)-ethyl]-urea;
1-[(R)-1-(4-Chloro-benzyl)-2-(4-cyclohexyl-4-propoxy-piperidin-1-yl)-2-oxo-ethyl]-3-[2-(1H-imidazol-4-yl)-ethyl]-urea; and their respective salts and enantiomers.

The most preferred MC1R agonist according to the invention is 4-Cyclohexyl-1-[(R)-2-{3-[2-(1H-imidazol-4-yl)-ethyl]-ureido}-3-(4-methoxy-phenyl)-propionyl]-piperidine-4-ethyl-carboxylate (Compound A).

The MC1R receptor agonist according to the invention is more preferably selected from compounds of general formula (II):

1-[(S)-2-[(S)-2-benzoylamino-3-(1H-imidazol-4-yl)-propionylamino]-3-(4-methoxy-phenyl)-propionyl]-3-phenyl-azetidin-3-yl-butyrate;
N—[(S)-1-[(S)-2-(3-Butoxy-3-o-tolyl-azetidin-1-yl)-1-(4-methoxy-benzyl)-2-oxo-ethylcarbamoyl]-2-(1H-imidazol-4-yl)-ethyl]-benzamide;
N—[(S)-1-[(S)-2-(3-Butoxy-3-phenyl-azetidin-1-yl)-1-(4-methoxy-benzyl)-2-oxo-ethylcarbamoyl]-2-(1H-imidazol-4-yl)-ethyl]-benzamide;
N—[(S)-1-[(S)-2-(3-Hydroxy-3-o-tolyl-azetidin-1-yl)-1-(4-methoxy-benzyl)-2-oxoethylcarbamoyl]-2-(1H-imidazol-4-yl)-ethyl]-benzamide;
1-[(S)-2-[(S)-2-benzoyl amino-3-(1H-imidazol-4-yl)-propionylamino]-3-(4-methoxy-phenyl)-propionyl]-3-o-tolyl-azetidin-3-yl-acetate;
1-[(S)-2-[(S)-2-benzoylamino-3-(1H-imidazol-4-yl)-propionylamino]-3-(4-methoxy-phenyl)-propionyl]-3-(4-fluoro-phenyl)-azetidin-3-yl-butyrate;
N—[(S)-1-[(S)-2-(3-Cyclohexyl-3-hydroxy-azetidin-1-yl)-1-(4-methoxy-benzyl)-2-oxo-ethylcarbamoyl]-2-(1H-imidazol-4-yl)-ethyl]-benzamide;
N—[(S)-1-[(S)-2-[3-Butoxy-3-(4-fluoro-phenyl)-azetidin-1-yl]-1-(4-methoxy-benzyl)-2-oxo-ethylcarbamoyl]-2-(1H-imidazol-4-yl)-ethyl]-benzamide;
N—[(S)-1-[(S)-2-[3-Butoxy-3-(3-fluoro-phenyl)-azetidin-1-yl]-1-(4-methoxy-benzyl)-2-oxo-ethylcarbamoyl]-2-(1H-imidazol-4-yl)-ethyl]-benzamide;
N—[(S)-2-(3-Cyclohexyl-3-hydroxy-azetidin-1-yl)-1-(4-methoxy-benzyl)-2-oxo-ethyl]-3-(1H-imidazol-4-yl)-propionamide;
N—[(S)-2-(3-Hydroxy-3-o-tolyl-azetidin-1-yl)-1-(4-methoxy-benzyl)-2-oxo-ethyl]-3-(1H-imidazol-4-yl)-propionamide;
N—[(R)-1-(3,4-Dichloro-benzyl)-2-(3-hydroxy-3-phenyl-azetidin-1-yl)-2-oxo-ethyl]-3-(1H-imidazol-4-yl)-propionamide;
N—[(S)-2-(3-Ethoxy-3-o-tolyl-azetidin-1-yl)-1-(4-methoxy-benzyl)-2-oxo-ethyl]-3-(1H-imidazol-4-yl)-propionamide;
N—[(S)-2-(3-Cyclopropylmethoxy-3-o-tolyl-azetidin-1-yl)-1-(4-methoxy-benzyl)-2-oxo-ethyl]-3-(1H-imidazol-4-yl)-propionamide;
N—[(R)-2-(3-Butoxy-3-o-tolyl-azetidin-1-yl)-1-(4-methoxy-benzyl)-2-oxo-ethyl]-3-(1H-imidazol-4-yl)-propionamide;
N—[(S)-2-(3-Butoxy-3-o-tolyl-azetidin-1-yl)-1-(4-methoxy-benzyl)-2-oxo-ethyl]-3-(1H-imidazol-4-yl)-propionamide;
N—[(R)-2-(3-Ethoxy-3-o-tolyl-azetidin-1-yl)-1-(4-methoxy-benzyl)-2-oxo-ethyl]-3-(1H-imidazol-4-yl)-propionamide;
N—[(R)-2-(3-Butoxy-3-phenyl-azetidin-1-yl)-1-cyclohexyl methyl-2-oxo-ethyl]-3-(1H-imidazol-4-yl)-propionamide
N—[(R)-2-(3-Butoxy-3-phenyl-azetidin-1-yl)-1-(2,4-dichloro-benzyl)-2-oxo-ethyl]-3-(1H-imidazol-4-yl)-propionamide;
N—[(R)-2-(3-Cyclopropylmethoxy-3-o-tolyl-azetidin-1-yl)-1-(4-methoxy-benzyl)-2-oxo-ethyl]-3-(1H-imidazol-4-yl)-propionamide;
N—[(S)-1-(4-Methoxy-benzyl)-2-oxo-2-(3-propoxy-3-o-tolyl-azetidin-1-yl)-ethyl]-3-(1H-imidazol-4-yl)-propionamide
N—[(R)-1-(4-Methoxy-benzyl)-2-oxo-2-(3-propoxy-3-o-tolyl-azetidin-1-yl)-ethyl]-3-(1H-imidazol-4-yl)-propionamide;
N—[(R)-2-[3-Butoxy-3-(4-fluoro-phenyl)-azetidin-1-yl]-1-(4-methoxy-benzyl)-2-oxo-ethyl]-3-(1H-imidazol-4-yl)-propionamide;
N—[(R)-1-(4-Methoxy-benzyl)-2-oxo-2-(3-pentyloxy-3-o-tolyl-azetidin-1-yl)-ethyl]-3-(1H-imidazol-4-yl)-propionamide;
N—[(R)-2-(3-Hexyloxy-3-o-tolyl-azetidin-1-yl)-1-(4-methoxy-benzyl)-2-oxo-ethyl]-3-(1H-imidazol-4-yl)-propionamide;
N—[(R)-1-(4-Methoxy-benzyl)-2-oxo-2-(3-pentyl-3-phenyl-azetidin-1-yl)-ethyl]-3-(1H-imidazol-4-A-propionamide;
N—[(R)-2-(3-Butyl-3-phenyl-azetidin-1-yl)-1-(4-methoxy-benzyl)-2-oxo-ethyl]-3-(1H-imidazol-4-A-propionamide;
N—[(R)-2-(3-Cyclopropylmethoxy-3-phenyl-azetidin-1-yl)-1-(4-methoxy-benzyl)-2-oxo-ethyl]-3-(1H-imidazol-4-yl)-propionamide;
N—[(R)-2-(3-Hydroxy-3-o-tolyl-azetidin-1-yl)-1-(4-methoxy-benzyl)-2-oxo-ethyl]-3-(1H-imidazol-4-yl)-propionamide;
N—[(R)-2-[3-Butoxy-3-(4-fluoro-phenyh-azetidin-1-yl]-1-(3-fluoro-benzyl)-2-oxo-ethyl]-3-(1H-imidazol-4-yl)-propionamide;
N—[(R)-2-[3-Butoxy-3-(4-fluoro-phenyh-azetidin-1-yl]-1-(4-fluoro-benzyl)-2-oxo-ethyl]-3-(1H-imidazol-4-A-propionamide
N—[(R)-2-(3-Butoxy-3-phenyl-azetidin-1-yl)-1-(4-fluoro-benzyl)-2-oxo-ethyl]-3-(1H-imidazol-4-yl)-propionamide;
N—{(R)-1-Benzyl-2-[3-butoxy-3-(4-fluoro-phenyh-azetidin-1-yl]-2-oxo-ethyl}-3-(4H-imidazol-2-yl)-propionamide;
N—[(R)-1-Benzyl-2-(3-butoxy-3-phenyl-azetidin-1-yl)-2-oxo-ethyl]-3-(1H-imidazol-4-yl)-propionamide;
N—[(R)-2-(3-Butoxy-3-phenyl-azetidin-1-yl)-1-(4-methoxy-benzyl)-2-oxo-ethyl]-3-(1H-imidazol-4-yl)-propionamide;
N—[(R)-1-(4-Methoxy-benzyl)-2-oxo-2-(3-pentyl-3-o-tolyl-azetidin-1-yl)-ethyl]-3-(1H-imidazol-4-yl)-propionamide;
N—[(R)-2-[3-(4-Fluoro-phenyl)-3-pentyl-azetidin-1-yl]-1-(4-methoxy-benzyl)-2-oxo-ethyl]-3-(1H-imidazol-4-yl)-propionamide;
N—[(R)-2-(3-Butoxy-3-o-tolyl-azetidin-1-yl)-1-(4-methoxy-benzyl)-2-oxo-ethyl]-3-(1H-[1,2,3]triazol-4-yl)-propionamide;
N—[(R)-2-(3-Butoxy-3-o-tolyl-azetidin-1-yl)-1-(4-methoxy-benzyl)-2-oxo-ethyl]-3-(5-methyl-3H-[1,2,4]triazol-3-yl)-propionamide;
N—[(R)-2-(3-Butoxy-3-o-tolyl-azetidin-1-yl)-1-(4-methoxy-benzyl)-2-oxo-ethyl]-3-(5-methyl-3H-imidazol-4-yl)-propionamide;
N—{(R)-1-(4-Methoxy-benzyl)-2-[3-(2-methoxy-phenyl)-3-pentyl-azetidin-1-yl]-2-oxo-ethyl}-3-(1H-imidazol-4-yl)-propionamide;
N—[(R)-2-[3-(2-Fluoro-phenyl)-3-pentyl-azetidin-1-yl]-1-(4-methoxy-benzyl)-2-oxo-ethyl]-3-(1H-imidazol-4-yl)-propionamide;
N—[(R)-2-[3-(2-Chloro-phenyl)-3-pentyl-azetidin-1-yl]-1-(4-methoxy-benzyl)-2-oxo-ethyl]-3-(1H-imidazol-4-yl)-propionamide;
N—[(R)-1-(4-Chloro-benzyl)-2-oxo-2-(3-pentyl-3-phenyl-azetidin-1-yl)-ethyl]-3-(1H-Imidazol-4-yl)-propionamide;

N—[(R)-1-(4-Fluoro-benzyl)-2-oxo-2-(3-pentyl-3-phenyl-azetidin-1-yl)-ethyl]-3-(1H-imidazol-4-yl)-propionamide;
N—[(R)-1-Benzyl-2-oxo-2-(3-pentyl-3-phenyl-azetidin-1-yl)-ethyl]-3-(1H-imidazol-4-yl)-propionamide;
N—[(R)-2-(3-Butoxy-3-o-tolyl-azetidin-1-yl)-1-(4-methoxy-benzyl)-2-oxo-ethyl]-3-(1H-imidazol-4-yl)-acrylamide;
N—[(R)-2-[3-(2,4-Difluoro-phenyl)-3-pentyl-azetidin-1-yl]-1-(4-methoxy-benzyl)-2-oxo-ethyl]-341 H-imidazol-4-yl)-propionamide;
N—[(R)-2-Oxo-2-(3-pentyl-3-phenyl-azetidin-1-yl)-1-(3-trifluoromethyl-benzyl)-ethyl]-3-(1H-imidazol-4-yl)-propionamide;
N—[(R)-2-Oxo-2-(3-pentyl-3-phenyl-azetidin-1-yl)-1-(4-trifluoromethyl-benzyl)-ethyl]-3-(1H-imidazol-4-yl)-propionamide;
N—[(R)-1-(3,4-Dichloro-benzyl)-2-oxo-2-(3-pentyl-3-phenyl-azetidin-1-yl)-ethyl]-3-(1H-imidazol-4-yl)-propionamide;
N—[(R)-1-(3,4-Difluoro-benzyl)-2-oxo-2-(3-pentyl-3-phenyl-azetidin-1-yl)-ethyl]-3-(1H-imidazol-4-yl)-propionamide;
N—[(R)-2-[3-(3,4-Dichloro-phenyl)-3-pentyl-azetidin-1-yl]-1-(4-methoxy-benzyl)-2-oxo-ethyl]-341 H-imidazol-4-yl)-propionamide;
N—[(R)-2-[3-(3-Fluoro-phenyl)-3-pentyl-azetidin-1-yl]-1-(4-methoxy-benzyl)-2-oxo-ethyl]-3-(1H-imidazol-4-yl)-propionamide;
N—[(R)-1-(3-Fluoro-benzyl)-2-oxo-2-(3-pentyl-3-phenyl-azetidin-1-yl)-ethyl]-3-(1H-imidazol-4-yl)-propionamide;
N—[(R)-1-(2-Fluoro-benzyl)-2-oxo-2-(3-pentyl-3-phenyl-azetidin-1-yl)-ethyl]-3-(1H-imidazol-4-yl)-propionamide;
N—[(R)-1-(2,4-Dichloro-benzyl)-2-oxo-2-(3-pentyl-3-phenyl-azetidin-1-yl)-ethyl]-3-(1H-imidazol-4-yl)-propionamide;
N—[(R)-2-[3-(4-Chloro-phenyl)-3-pentyl-azetidin-1-yl]-1-(4-methoxy-benzyl)-2-oxo-ethyl]-3-(1H-imidazol-4-yl)-propionamide;
N—[(R)-2-[3-(2,5-Difluoro-phenyl)-3-pentyl-azetidin-1-yl]-1-(4-methoxy-benzyl)-2-oxo-ethyl]-341 H-imidazol-4-yl)-propionamide;
N—[(R)-2-[3-(2,6-Difluoro-phenyl)-3-pentyl-azetidin-1-yl]-1-(4-methoxy-benzyl)-2-oxo-ethyl]-341 H-imidazol-4-yl)-propionamide;
N-[2-(3-Butoxy-3-o-tolyl-azetidin-1-yl)-1-(4-methoxy-benzyl)-2-oxo-ethyl]-3-(1H-imidazol-4-yl)-hexyramide;
N-[2-(3-Butoxy-3-o-tolyl-azetidin-1-yl)-1-(4-methoxy-benzyl)-2-oxo-ethyl]-3-(1H-imidazol-4-yl)-pentyramide;
N—[(R)-1-(4-Methoxy-benzyl)-2-oxo-2-(3-pentyl-3-phenyl-azetidin-1-yl)-ethyl]-3-(3-methyl-3H-imidazol-4-yl)-propionamide;
N-[2-(3-Butoxy-3-o-tolyl-azetidin-1-yl)-1-(2,4-dichloro-benzyl)-2-oxo-ethyl]-3-(1H-imidazol-4-yl)-hexyramide;
N—[(R)-2-(3-Cyclohexyl-3-pentyl-azetidin-1-yl)-1-(4-methoxy-benzyl)-2-oxo-ethyl]-3-(1H-imidazol-4-yl)-propionamide;
N—[(R)-2-(3-Butoxy-3-o-tolyl-azetidin-1-yl)-1-(4-methoxy-benzyl)-2-oxo-ethyl]-3-(3-methyl-3H-imidazol-4-yl)-propionamide;
3-(1H-Imidazol-4-yl)-N—[(R)-1-(4-methoxy-benzyl)-2-oxo-2-(3-phenyl-azetidin-1-yl)-ethyl]-propionamide;
N—[(R)-2-[3-(4-Fluoro-phenyl)-azetidin-1-yl]-1-(4-methoxy-benzyl)-2-oxo-ethyl]-3-(1H-imidazol-4-yl)-propionamide;
3-(1H-Imidazol-4-yl)-N—{(R)-1-(4-methoxy-benzyl)-2-[3-(2-methoxy-phenyl)-azetidin-1-yl]-2-oxo-ethyl}-propionamide;
N—[(R)-2-[3-(2-Fluoro-phenyl)-azetidin-1-yl]-1-(4-methoxy-benzyl)-2-oxo-ethyl]-3-(1H-imidazol-4-yl)-propionamide;
3-(1H-Imidazol-4-yl)-N—{(R)-1-(4-methoxy-benzyl)-2-oxo-2-[3-phenyl-3-(4,4,4-trifluoro-butyl)-azetidin-1-yl]-ethyl}-propionamide;
N—[(R)-2-[3-(5-Fluoro-pentyl)-3-phenyl-azetidin-1-yl]-1-(4-methoxy-benzyl)-2-oxo-ethyl]-3-(1H-imidazol-4-yl)-propionamide;
N—[(R)-2-(3-Cyclopropyl-3-phenyl-azetidin-1-yl)-1-(4-methoxy-benzyl)-2-oxo-ethyl]-3-(1H-imidazol-4-yl)-propionamide;
N—[(R)-2-(3-Cyclopropylmethyl-3-phenyl-azetidin-1-yl)-1-(4-methoxy-benzyl)-2-oxo-ethyl]-3-(1H-imidazol-4-yl)-propionamide;
(S)-2-Hydroxy-3-(1H-imidazol-4-yl)-N-[1-(4-methoxy-benzyl)-2-oxo-2-(3-propoxy-3-o-tolyl-azetidin-1-yl)-ethyl]-propionamide;
(S)-2-Amino-3-(1H-imidazol-4-yl)-N-[1-(4-methoxy-benzyl)-2-oxo-2-(3-propoxy-3-o-tolyl-azetidin-1-yl)-ethyl]-propionamide;
N-[2-(3-Butoxy-3-o-tolyl-azetidin-1-yl)-1-(4-methoxy-benzyl)-2-oxo-ethyl]-3-(1H-imidazol-4-yl)-butyramide;
(S)—N-[2-(3-Butoxy-3-phenyl-azetidin-1-yl)-1-(4-methoxy-benzyl)-2-oxo-ethyl]-3-(1H-imidazol-4-yl)-2-methanesulfonylamino-propionamide;
N—[(R)-1-(4-Methoxy-benzyl)-2-oxo-2-(3-pentyl-3-phenyl-azetidin-1-yl)-ethyl]-3-(1-methyl-1H-imidazol-4-yl)-propionamide;
N—[(R)-2-[3-(4-Hydroxy-butoxy)-3-o-tolyl-azetidin-1-yl]-1-(4-methoxy-benzyl)-2-oxo-ethyl]-3-(-1H-imidazol-4-yl)-propionamide;
N—[(R)-2-(3-Cyclopropylmethoxy-3-o-tolyl-azetidin-1-yl)-1-(4-methoxy-benzyl)-2-oxo-ethyl]-345-methyl-1H-imidazol-4-yl)-propionamide;
and their respective salts and enantiomers.

In another embodiment the compound is preferentially selected from:
N—[(R)-2-[3-(4-Hydroxy-butoxy)-3-o-tolyl-azetidin-1-yl]-1-(4-methoxy-benzyl)-2-oxo-ethyl]-3-(-1 H-imidazol-4-yl)-propionamide,
N—[(R)-2-(3-Cyclopropylmethoxy-3-o-tolyl-azetidin-1-yl)-1-(4-methoxy-benzyl)-2-oxo-ethyl]-3-(5-methyl-1H-imidazol-4-yl)-propionamide (compound B);
and their respective salts and enantiomers.

Advantageously, the system according to the invention comprises a composition wherein the MC1R receptor agonist at a concentration between about 0.001 and 10% by weight, and, in particular 0.005%, 0.01%. 0.05%, 0.1%, 0.5%, 1%, 5%, preferably between 0.005 and 5%, more preferably 1% by weight, based on the total weight of the composition comprising it.

Accordingly, the composition comprises, in a cosmetically acceptable medium, at least one MC1R agonist, preferentially at least a compound of general formula (I) or (II).

By Cosmetically acceptable medium it is meant a medium compatible with the skin, mucous membranes and nails.

The further example illustrates the invention without reducing the scope of this latter.

EXAMPLE

In Vivo Measure of Pro-Pigmenting Activity of 2 MC1R Agonists by Topical Route in Mice In mice, melanocytes are not present in the epidermis of hair-covered areas but are mainly present in the hair follicles. Pigmentation can be induced by irradiation with UVB in combination with topical or oral agents. The pigmentation changes can be quantified by various means such as clinical score pigmentation and pigmentation measurement by image analysis.

The evaluation of the MC1R receptor agonists pro-pigmenting activity in combination with NB-UVB irradiation (60 mJ/cm2) is performed by topical application on the back of the mouse SKH2 during 43 days with MC1R agonist compound A at 8% or MC1R agonist compound B at 8% in combination with NB-UVB radiation.

Practically, the animals were irradiated using the system Biospectra equipped NB-UVB lamps (peak emission maximum at 312 nm) irradiation at 3 times per week at 60 mJ/cm$^2$ on Monday, Wednesday and Friday. The treatment is carried out 5 days a week and 50 µl of the test product (compounds A or B) is diluted in the vehicle and applied on the back. In the case of associations with radiation, the compounds are administered after irradiation.

Then, the pigmentation changes is quantified by clinical score pigmentation and pigmentation measurement by image analysis.

Clinical Score of Pigmentation

The clinical score of animals is performed 1 time per week before irradiation. The pigmentation is evaluated with a score on a scale of 0 to 4. The distribution of scores is as follows:
0: natural pigmentation
1: slight pigmentation
2: moderate pigmentation
3: marked pigmentation
4: intense pigmentation The following calculations are performed:
Mean± sem-clinical scores per week treatment group
Aires under the curve (AUC) scores clinical animal J1 to J43.
Index increased AUC for each combination group versus the non-irradiated group versus vehicle and vehicle-irradiated.

The AUC is obtained by summing the areas of the rectangles between the first and last day of the study. The different treatment groups were compared to the vehicle group and UVB irradiated+vehicle group on this parameter using a Student t test.

Quantification of Pigmentation by Image Analysis at the End of Study:

At the end of the study, for each animal, two digital photographs of the skin of the back are made with a high quality dermascope and digital camera such as the Lite-Scope™. The determination of the surface and the average pixel intensity is pigmented obtained by image analysis and the level of pigmentation is obtained by the product of two values.

The following calculations are performed:
Mean±sem of pigmentation by image analysis by treatment group
Increased pigmentation Index by image analysis for each combination group versus the non-irradiated group versus vehicle and vehicle-irradiated.

Figure 1:
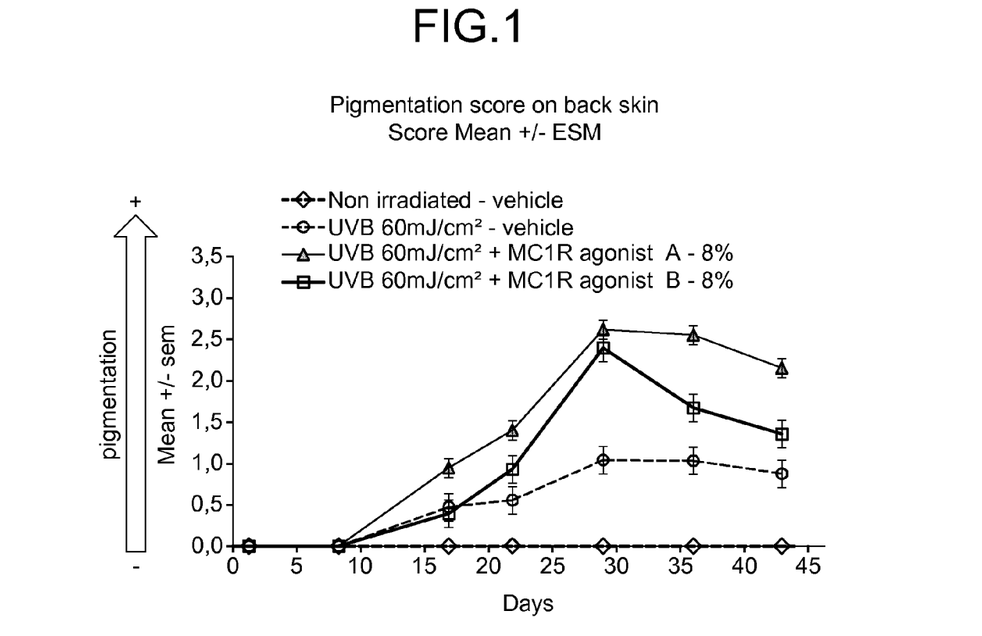
Figure 2:
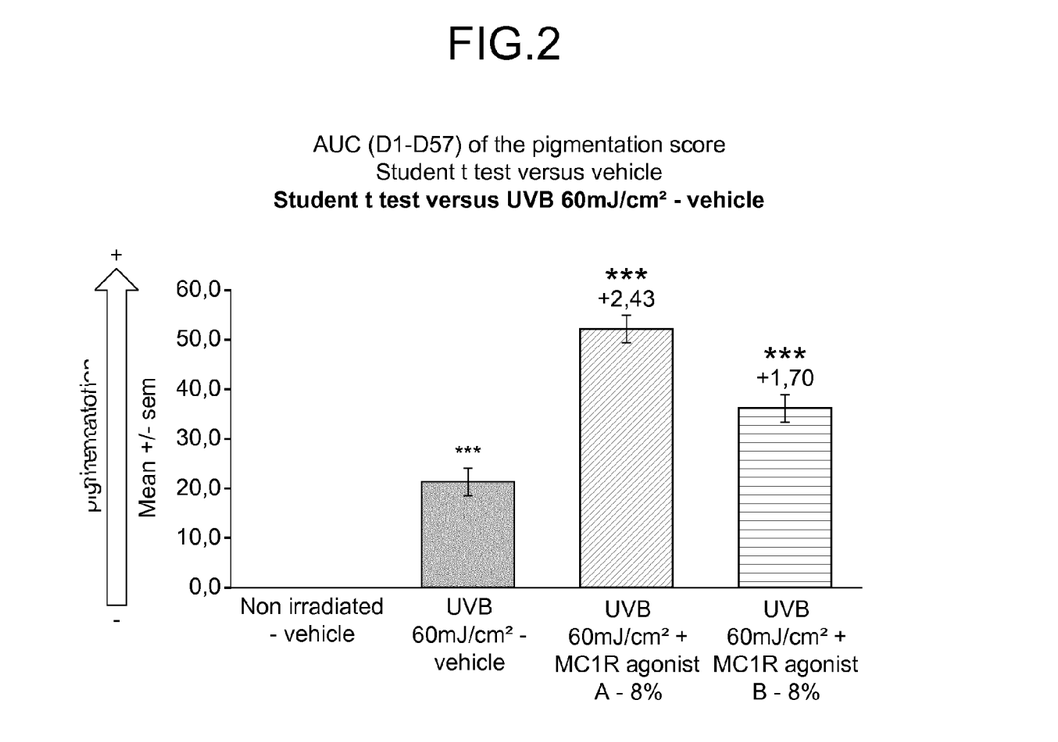

Results:
The results are shown in FIGS. 1, 2 and 3
The results presented in FIGS. 1 and 2 show that repeated irradiation with NB-UVB (60 mJ/cm2) causes a moderate pigmentation on the backs of SKH2 mice. Treatment with the MC1R agonist A at 8% or MC1R agonist B at 8%, in combination with NB-UVB irradiation (60 mJ/cm2) significantly increases the pigmentation of the skin from the irradiated group treated with the vehicle.

Figure 3:
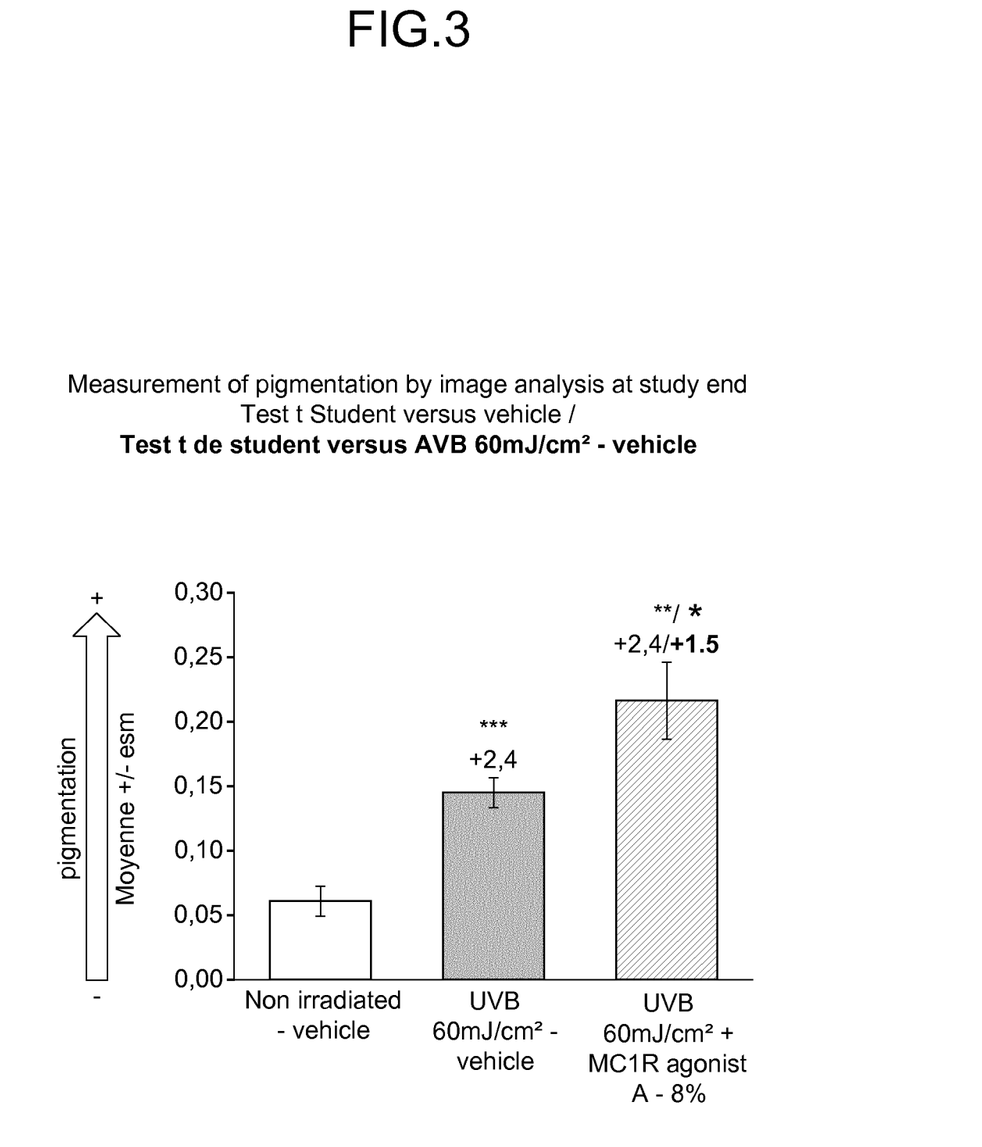

This synergistic effect is confirmed by the objective assessment of the pigmentation level at the end of the study by image analysis (FIG. 3) for MC1R agonist A compound.

The invention claimed is:

1. A system comprising a combination of at least one MC1R receptor agonist and a source of NB-UVB, wherein said system is adapted for simultaneous or sequential use of said MC1R receptor agonist and said NB-UVB in amounts effective for the treatment of dermatological conditions linked to a hypopigmentation,
wherein said MC1R agonist is N-[((R)-2-[3-(4-hydroxybutoxy)-3-o-tolyl-azetidin-1-yl]-1-(4-methoxybenzyl)-2-oxo-ethyl]-3-(1H-imidazol-4-yl)-propionamide or N—[(R)-2-(3-cyclopropylmethoxy-3-o-tolyl-azetidin-1-yl)-1-(4-methoxybenzyl)-2-oxo-ethyl]-3-(5-methyl-1H-imidazol-4-yl)-propionamide,
and
wherein said source of NB-UVB has a wavelength between 280 nm and 315 nm.

2. The system according to claim 1, wherein said MC1R agonist is present in a composition applied topically or administered orally.

3. The system according to claim 2, wherein said composition comprises, in a cosmetically acceptable medium, at least one MC1R agonist.

4. The system according to claim 2, wherein said MC1R agonist is present in the composition at a concentration between about 0.001% and 10% by weight based on the total weight of the composition comprising it.

5. The system according to claim 1, wherein the skin disease associated with hypopigmentation is selected from the group consisting of vitiligo, albinism, hypomelanoses, depigmentation by physical or chemical agents, post-inflammatory hypopigmentation, phenomenon of Sutton and other hypopigmentation lesions.

6. A method of treating a dermatological condition linked to a hypopigmentation, the method comprising administering to an individual subject in need thereof a composition comprising at least one MC1R receptor agonist in combination with NB-UVB,
wherein said MC1R agonist is N-[(R)-2-[3-(4-hydroxybutoxy)-3-o-tolyl-azetidin-1-yl]-1-(4-methoxybenzyl)-2-oxo-ethyl]-3-(1H-imidazol-4-yl)-propionamide or N—[(R)-2-(3-cyclopropylmethoxy-3-o-tolyl-azetidin-1-yl)-1-(4-methoxybenzyl)-2-oxo-ethyl]-3-(5-methyl-1H-imidazol-4-yl)-propionamide,
and
wherein said source of NB-UVB has a wavelength between 280 nm and 315 nm.

7. A method of treating a dermatological condition linked to hypopigmentation, the method comprising applying to an affected or susceptible area, a combination of at least one MC1R receptor agonist and NB-UVB for simultaneous or sequential in time treatment of the dermatological condition,
wherein said MC1R agonist is N-[((R)-2-[3-(4-hydroxybutoxy)-3-o-tolyl-azetidin-1-yl]-1-(4-methoxybenzyl)-2-oxo-ethyl]-3-(1H-imidazol-4-yl)-propionamide or N—[(R)-2-(3-cyclopropylmethoxy-3-o-tolyl-azetidin-1-yl)-1-(4-methoxybenzyl)-2-oxo-ethyl]-3-(5-methyl-1H-imidazol-4-yl)-propionamide,
and
wherein said source of NB-UVB has a wavelength between 280 nm and 315 nm.

8. The method according to claim 7, wherein the skin disease associated with hypopigmentation is selected from the group consisting of vitiligo, albinism, hypomelanoses, depigmentation by physical or chemical agents, post-inflammatory hypopigmentation, phenomenon of Sutton and other hypopigmentation lesions.

9. A product containing a composition comprising at least one MC1R receptor agonist for use in combination with NB-UVB, as a medicament for simultaneous or sequential in time treatment of dermatological conditions linked to a hypopigmentation, wherein said MC1R agonist is N-[((R)-2-[3-(4-hydroxy-butoxy)-3-o-tolyl-azetidin-1-yl]-1-(4-methoxybenzyl)-2-oxo-ethyl]-3-(1H-imidazol-4-yl)-propionamide or N—[(R)-2-(3-cyclopropylmethoxy-3-o-tolyl-azetidin-1-yl)-1-(4-methoxybenzyl)-2-oxo-ethyl]-3-(5-methyl-1H-imidazol-4-yl)-propionamide, and wherein said source of NB-UVB has a wavelength between 280 nm and 315 nm.

10. The system according to claim 1, wherein the NB-UVB length wave is between 305 nm and 310 nm.

11. The system according to claim 1, wherein the NB-UVB length wave is between 307 nm and 309 nm.

12. The method according to claim 6, wherein the NB-UVB length wave is between 305 nm and 310 nm.

13. The method according to claim 6, wherein the NB-UVB length wave is between 307 nm and 309 nm.

14. The method according to claim 7, wherein the NB-UVB length wave is between 305 nm and 310 nm.

15. The method according to claim 7, wherein the NB-UVB length wave is between 307 nm and 309 nm.

* * * * *